United States Patent [19] [11] 4,277,421
Landauer et al. [45] Jul. 7, 1981

[54] PROCESS FOR THE MANUFACTURE OF PARA-TERT.BUTYLBENZALDEHYDE AND ITS DERIVATIVES WHICH ARE HALOGEN-SUBSTITUTED AT THE NUCLEUS

[75] Inventors: Franz Landauer, Frankfurt am Main; Georg Schaeffer, Hofheim, both of Fed. Rep. of Germany

[73] Assignee: Hoechst Aktiengesellschaft, Frankfurt am Main, Fed. Rep. of Germany

[21] Appl. No.: 94,058

[22] Filed: Nov. 14, 1979

[30] Foreign Application Priority Data

Nov. 16, 1978 [DE] Fed. Rep. of Germany ....... 2849692
Mar. 22, 1979 [DE] Fed. Rep. of Germany ....... 2911237

[51] Int. Cl.$^3$ .................... C07C 25/02; C07C 45/43
[52] U.S. Cl. .................................. 570/185; 568/437; 570/127
[58] Field of Search ............... 260/599, 600 R, 651 R, 260/651 F; 568/437

[56] References Cited

U.S. PATENT DOCUMENTS 3,700,736 10/1972 Yamamoto et al. .................. 260/599
4,085,147 4/1978 Rosinger et al. ................. 260/600 R
4,108,904 8/1978 Brown et al. ..................... 260/600 R

FOREIGN PATENT DOCUMENTS 2163741 7/1973 France ..................................... 568/437
52-25733 Japan ..................................... 568/437
816253 7/1959 United Kingdom ..................... 568/437

OTHER PUBLICATIONS

Koike et al., Chem. Abst., vol. 87, #84685, (1977).
Morris et al., Organic Chemistry, 2nd ed., pp. 386-390 (1966).
Voronkor et al., Chem. Abst., vol. 78, #71582n (1973).
Pearson et al., Chem. Abst., vol. 86, #55196z (1977).
Foldesi, Chem. Abst., vol. 65, #8806c (1966).
Bevan, Chem. Abst., vol. 54, #14244b (1957).

Primary Examiner—Natalie Trousof
Assistant Examiner—James H. Reamer
Attorney, Agent, or Firm—Curtis, Morris & Safford

[57] ABSTRACT p-tert.Butylbenzaldehyde and the derivatives thereof which are halogen-substituted at the nucleus are prepared by bromination of p-tert.butyltoluene and the derivatives thereof which are correspondingly halogen-substituted at the nucleus under side-chain halogenation conditions until the benzal bromide is obtained which is then saponified. Practically no undesired bromination at the nucleus or the tert.butyl group takes place.

The products obtained are valuable intermediates for the manufacture of pharmaceutical agents, plant protecting agents and dyestuffs.

3 Claims, No Drawings

PROCESS FOR THE MANUFACTURE OF PARA-TERT.BUTYLBENZALDEHYDE AND ITS DERIVATIVES WHICH ARE HALOGEN-SUBSTITUTED AT THE NUCLEUS

This invention relates to a process for the manufacture of p-tert.butylbenzaldehyde and of its derivatives which are halogen-substituted at the nucleus; it further relates to p-tert.butylbenzal bromide and its derivatives which are halogen-substituted at the nucleus, which are formed as intermediates.

p-tert.Butylbenzaldehyde and its derivatives which are halogen-substituted at the nucleus are valuable intermediates for the manufacture of pharmaceutical agents, plant protecting agents, dyestuffs and perfumes.

p-tert.Butylbenzaldehyde and its derivatives are produced by methods generally known for the manufacture of aromatic aldehydes. These compounds can be obtained, for example, by reacting tert.butylbenzene with CO/HCl in the presence of CuCl. The main drawback of these methods is, however, the necessity to use a Cu salt requiring a special waste water purification.

In another known process in which a Cu salt is likewise used, i.e. $Cu(NO_3)_2$, p-tert.butyltoluene is the starting material, which is first reacted with an approximately equivalent amount of bromine to give p-tert.butylbenzyl bromide which is then boiled for a prolonged period of time in combination with a $Cu(NO_3)_2$ solution. p-tert.Butylbenzaldehyde is obtained in this manner in a yield of about 42% of the theory (cf. J. Chem. Soc., 1935, page 1848).

In another known process for the conversion of p-tert. butylbenzyl bromide into p-tert.butylbenzaldehyde the $Cu(NO_3)_2$ solution of the latter method is replaced by a solution of hexamethylene tetramine in aqueous ethanol (Sommelet reaction, J. Chem. Soc., 1940, page 702). In this reaction, a mixture of methylamine, ammonia and formaldehyde is obtained from the hexamethylene tetramine, which has to be eliminated for reasons of environmental protection. Therefore, this process requires, in addition to the two other processes mentioned above involving a Cu salt, a complicated and expensive waste water purification. Moreover, all the aforesaid processes are characterized by a high energy demand and their spacetime-yields are not satisfactory.

The use of another method known for the manufacture of aromatic aldehydes (saponification of benzal chlorides with water, cf. DE-OS No. 2,044,832) for the manufacture of p-tert.butylbenzaldehyde proved to be little successful as ascertained by the experiment described in the Comparative Example, as follows, since in the manufacture of the required p-tert.butylbenzal chlorides, by free radical initiated chlorination of p-tert.butyltoluene, products are obtained the organically bound chlorine of which can be split off partially only under the usual conditions of alkaline hydrolysis (cf. Houben-Weyl, Methoden der Org. Chemie, volume II, page 233, Stuttgart 1953), which indicates a rather significant chlorination at the nucleus. This is, of course, not desired when pure p-tert.butylbenzaldehyde shall be the final product. Derivatives, substituted by chlorine at the nucleus, of p-tert.butylbenzaldehyde are wanted sometimes for the manufacture of pharmaceutical agents, plant protecting agents, dyestuffs and perfumes, but in these cases the chlorine should be bound in defined position like the other halogens (F, Br, I) prior to the halogenation of the side chain.

It is therefore, an object of the present invention to provide a process for the manufacture of p-tert.butylbenzaldehyde and its derivatives which are halogen-substituted at the nucleus, which obviates the disadvantages of the known processes, that is to say, which does not necessitate an expensive waste water purification, which gives good yields of the desired product, in which substituted by-products are not formed to an undesired extent, and which is economical.

This objective is achieved in simple and excellent manner by first preparing the corresponding benzal bromide from p-tert.butyltoluene, or a derivative thereof which is halogen-substituted at the nucleus, by bromination of the side chain, and then saponifying the product obtained to the desired aldehyde.

The present invention, therefore, provides a process for the manufacture of p-tert.butylbenzaldehyde and its derivatives which are halogen-substituted at the nucleus, which comprises (a) reacting p-tert.butyltoluene and the derivatives thereof which are halogen-substituted at the nucleus with approximately 2 mols of bromine/mol of organic starting compound, at a temperature of from about 40° to 200° C., preferably about 40° to 120° C., optionally under the action of high energy radiations or in the presence of radical-forming agents and (b) saponifying with water the p-tert.butylbenzal bromide and the derivatives thereof which are halogen-substituted at the nucleus, obtained, optionally after their isolation at elevated temperature, if desired in the presence of the usual saponification catalysts.

Suitable starting products in the process according to the invention are p-tert.butyltoluene and the derivatives substituted, preferably monosubstituted, at the nucleus by halogen. The mono-substituted derivatives can be illustrated by the following formula I

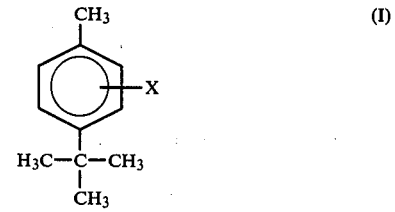

in which X denotes F, Cl, Br or I, preferably F, Cl or Br.

The respective starting compound is reacted with about 2 (from 1.8 to 2.2 and preferably 1.9 to 2.1) mols of bromine for each mol of starting compound, at about 40° to 200° C., preferably 40° to 120° C., optionally under the action of high energy radiation, preferably ultraviolet light, or in the presence of free radical-forming agents.

Suitable radical-forming agents are organic peroxides and azoisobutyronitrile as generally used in chlorination reactions of side chains.

High energy radiation or the presence of radical-forming agents is not absolutely necessary for the success of the reaction, but each greatly accelerates same and, therefore, has an advantageous effect.

The bromine can be added dropwise in liquid form or introduced in gaseous form after evaporation. In the latter case an inert gas, for example $N_2$ or argon, may be added. The bromination can be carried out without as well as with a suitable solvent, such as an inert hydrocarbon, preferably halogenated hydrocarbons, for example carbon tetrachloride or o-dichlorobenzene. The reaction can be carried out with or without application of pressure, discontinuously as well as continuously in a suitable apparatus.

The p-tert.butylbenzal bromide and nucleus-substituted derivatives thereof obtained when derivatives, halogen-substituted at the nucleus, of p-tert.butyltoluene are used as starting material, do not have undesired bromine substituents at the aromatic nucleus and constitute novel compounds having the formula II

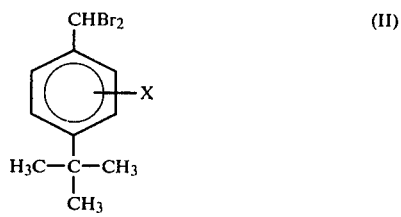

in which X denotes H, F, Cl, Br or I, preferably H, F, Cl or Br and more preferably H.

Thus, compounds of the aforesaid formula are,

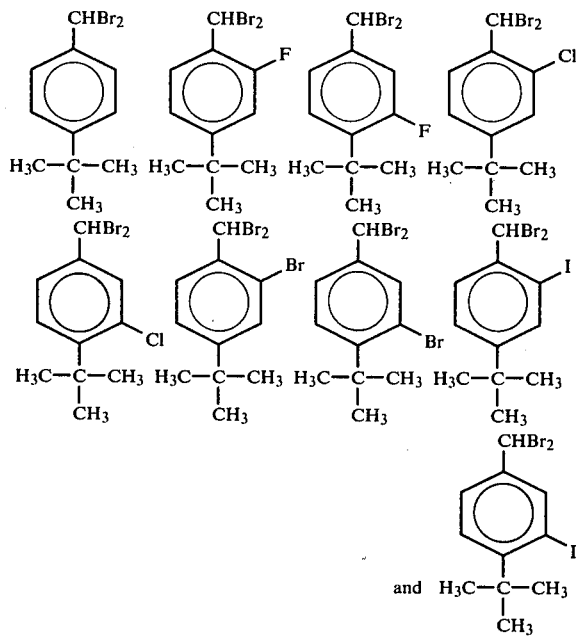

For saponifying the compounds of formula II to give the corresponding benzaldehyde, these compounds can be isolated and purified (for example by recrystallization) or they can be saponified without isolation.

The saponification is carried out by any method known for the saponification of benzal halides at elevated temperatures, preferably at about 60° to 150° C., more preferably about 80° to 120° C., with water, optionally in the presence of the usual saponification catalysts, for example metal halides such as $FeCl_3$ and $ZnBr_3$ or also $H_2SO_4$ and the like. It proved advantageous to use 1 mol of water for each mol of benzal bromide (II). It is likewise possible to use an excess amount of water, but in this case the aqueous phase has to be separated. In general, water is added to the benzal bromide (+ saponification catalyst) at the rate at which hydrogen bromide is formed and can be absorbed.

The saponification can be carried out at atmospheric pressure as well as under elevated pressure. Inert solvents may also be added, for example, hydrocarbons or chlorohyrocarbons. The use of emulsifiers, which ensure a good mixing of the organic phase with the water added, is also possible.

The hydrogen bromide formed in the process of the invention is preferably absorbged in a conventional absorption device. It can be directly used for other chemical reactions or it can be sold.

In the process of the invention p-tert.butylbenzaldehyde and the derivatives thereof substituted by halogen at the nucleus are obtained in excellent yields. They have the formula III

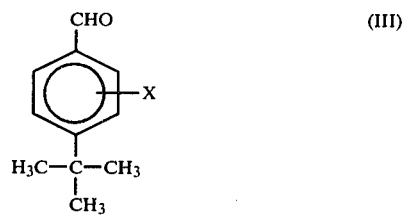

in which X denotes H, F, Cl, Br or I, preferably H, F, Cl or Br and more preferably H.

Besides the substituents at the nucleus present in the starting products they do not contain other undesired (bromine) substituents, which is extremely surprising as, usually, halogenations with chlorine and bromine normally take an identical course and, with side chain chlorination of p-tert.butyltoluene, a considerable chlorination at the nucleus cannot be avoided. In contradistinction thereto, in the bromination of p-tert.butyltoluene and of the corresponding substitution products thereof no or substantially no undesired halogenation at the nucleus and no bromination of the tert.butyl group take place.

The high selectivity and yield obtained with the process of the invention and the fact that as, compared with some processes of the state of the art, no special purification of the waste water is required, represent considerable progress.

In spite of the favorable and selective course of the reaction it may happen, even if almost exactly the stoichiometric amount (2 mols) of bromine is used for each mol of organic starting compound (p-tert.butyltoluene or a corresponding nucleus-substituted derivative thereof), that a small amount of benzyl bromide and also benzotribromide is formed in the bromination. In the subsequent saponification in which the desired aldehyde is obtained from the main bromination product (benzal bromide), the benzyl bromide obtained as by-product is not saponified and remains unchanged in the reaction mixture. The benzotribromide by-product, however, is saponified to give the corresponding benzoic acid, which may be readily eliminated by extraction with a mild alkali.

The small amounts of benzyl bromide possibly contained in the aldehyde and not susceptible of saponification can be removed, practically speaking only by a repeated and expensive rectification under reduced pressure. For many applications of the aldehyde small amounts of benzyl bromide as impurity do not have an adverse effect; for other applications, however, for example if the aldehyde is to be used in the perfume industry or as as intermediate for the manufacture of pharmaceutical agents, an almost 100% purity is required and thus a quantitative removal of the benzyl bromide contained in the aldehyde is indispensable. Moreover, p-tert.butylbenzaldehyde containing traces of p-tert.butylbenzyl bromide changes its color more rapidly on standing then the pure aldehyde.

According to a special variant of the process according to the invention, substantially pure p-tert.butylbenzaldehyde and derivatives thereof which are halogen-substituted at the nucleus, especially compounds which do not contain benzyl bromide, can be obtained by adding, during or after saponification according to stage b), a small amount of formaldehyde and ammonia ($CH_2 + NH_3$) or of hexamethylene tetramine in aqueous solution and heating the mixture.

In this manner the benzyl bromide present as by-product is converted into the corresponding aldehyde (Sommelet reaction).

If $CH_2O + NH_3$ or hexamethylene tetramine is added during saponification, the reaction mixture containing same should be kept at the saponification temperature (preferably about 60° to 150° C., more preferably about 80° to 120° C.) for a further one to several hours. Because the saponification is carried out in aqueous solution, the water normally required for the conversion of the corresponding benzyl bromide into the aldehyde is contained in the reaction mixture. If the amount of water present is insufficient for saponification, further water should be added.

Preferably, however, the corresponding benzyl bromide is converted into the aldehyde after saponification, either in the saponification mixture after completion of the reaction or after isolation of the benzaldehyde containing the by-product. It proved important in either case to react $CH_2O + NH_3$ or hexamethylene tetramine in aqueous solution with the benzyl bromide to be converted into the aldehyde for a prolonged period of time, normally about 1 to several hours, at elevated temperature, preferably at about 60° to 150° C., more preferably about 80° to 120° C.

The amount of $CH_2O + NH_3$ can be equimolar to the amount of benzyl bromide by-product, determined, for example by gas chromatography (1 mol $CH_2O + 1$ mol $NH_3$ per mol of benzyl bromide). It is preferred, however, to add $CH_2O$ and $NH_3$ in an excess, for example about 1.1 to 4 mols, preferably 1.1 to 2 mols, of $CH_2O$ and the same molar amount of $NH_3$ for each mol of p-tert.butylbenzyl bromide or its halogen-substituted derivative. Instead of the specified amounts of $CH_2O + NH_3$, equivalent amounts of hexamethylene tetramine can also be used, of course, which is even preferred.

The Sommelet reaction to be carried out during or after the saponification stage of the process can be performed at atmospheric pressure as well as under pressure.

When the Sommelet reaction is terminated, the reaction mixture is first extracted with a mild alkali in order to remove p-tert.butylbenzoic acid or the halogen-substituted derivative thereof and the pure aldehyde is then obtained from the residue by vacuum distillation.

It has surprisingly been found that when carrying out the process as described above the organic solvents and diluents (alcohols, $CHCl_3$, acetic acid and the like; cf. Weygand/Hilgetag, Organisch-Chemische Experimentierkunst, Verlag Johann Ambrosium Barth, Leipzig, 1970, page 346) normally used in the Sommelet reaction are not necessary, which means a considerable advantage in that no expensive apparatus for separation and recovery need be used.

It is thus possible to produce in simple manner pure p-tert.butylbenzaldehyde and the derivatives thereof which are halogen-substituted at the nucleus without using expensive rectification apparatus. As compared with the pure Sommelet reaction using p-tert.butylbenzyl bromide and the derivatives thereof which are halogen-substituted at the nucleus, this process variant has the advantage that only a relatively small amount of $CH_2O + NH_3$ or hexamethylene diamine must be used and, therefore, the main drawback had mentioned above (waste water stongly contaminated with $CH_2O + NH_3$ or $NH_4Br$) is practically done away with.

Hence, the process is economic and does not have a polluting effect on the environment. Due to the conversion of the benzyl bromide by-product into the desired aldehyde, the aldehyde yield is above that obtainable without the special variant of the process described above.

The following examples illustrate the invention. After the examples according to the invention a comparative example is given in which chlorine was used instead of bromine as halogenationagent for p-tert.butyltoluene.

EXAMPLE 1

In a 1 liter, four-necked flask provided with stirrer, thermometer, dropping funnel and reflux condenser and connected with an adsorbing device filled with water for hydrogen bromide, 296 g (2 mols) of p-tert.butyltoluene were heated to 100° to 110° C. With radiation by ultraviolet light 656 g of bromine (4.1 mols) were added dropwise during the course of 3.5 hours. The hydrogen bromide still contained in the reaction mixture was then blown out by means of nitrogen.

Yield of crude p-tert.butylbenzal bromide: 606 g (98.7% of the theory). The total bromine found was 53.3%; saponifiable bromine found 53.4%, that calculated was 52.3%.

The same good yield was obtained when gaseous bromine was introduced into the starting compound.

The pure p.tert.butylbenzal bromide melted at 44° C. (recrystallized from ethanol).

0.6 g. of $ZnCl_2$ and 0.3 g of water were added to the crude p-tert.butylbenzal bromide, the mixture was heated to 110° C., and 36 g of water were dropped in over a period of 4 hours while the reaction temperature was gradually reduced to 90° to 100° C. The hydrogen bromide formed in the saponification was absorbed in the water of the series-connected apparatus.

After the addition of the water, stirring of the mixture was continued for 30 minutes and the remainder of hydrogen bromide was blown out with nitrogen. 316 g (97.5% of the theory) of hydrogen bromide were recovered.

The crude p-tert.butylbenzaldehyde was then distilled under reduced pressure. It had a boiling point of 90° C. under 3 torr.

Yield: 299 g or 92.5% of the theory (=1.85 mols).

EXAMPLE 2

Under the conditions specified in Example 1 crude p-tert.butylbenzaldehyde was prepared from 2 mols of p-tert.-butyltoluene and 0.4 mols of bromine, and the p-tert.butylbenzyl bromide contained therein was converted into the aldehyde according to the process variant described above.

As found by gas chromatographic analysis, the crude p-tert.butylbenzaldehyde still contained 7.3% of p-tert.-butylbenzyl bromide.

A solution of 19 g of hexamethylene tetramine in 40 g of H₂O was added to the crude aldehyde and the mixture was stirred for 2 hours at 100° to 110° C.

As determined by gas chromatographic analysis the product treated in this manner then contained less than 0.3% of p-tert.butylbenzyl bromide.

To extract the p-tert.butylbenzoic acid the reaction mixture was stirred with aqueous soda solution. After acidification of the separated aqueous solution with hydrochloric acid, p-tert.butylbenzoic acid was precipitated. 12 g of acid were obtained.

The crude aldehyde was distilled under reduced pressure. It boiled at 110° C. under 10 torr. Yield: 310 g or 95.6% of the theory.

EXAMPLE 3

In a 250 ml glass flask 100 g, or 0.548 mol, of 1-methyl-2-chloro-4-tert.butylbenzene was reacted, with UV radiation and while stirring, with 175.5 g or 1.097 mols, of bromine under the following conditions:

first 100 g, or 0.625 mol, of liquid bromine were added dropwise at a reaction temperature of 130° C. over a period of 60 minutes. The reaction temperature was then raised to 180° C. and a further 75.5 g, or 0.472 mol, of bromine were dropped in. Stirring of the mixture was continued for 30 minutes at 180° C. The reaction mixture was cooled to 20° C. and small amounts of hydrogen bromide and bromine dissoved in the mixture were removed by passing through nitrogen.

After blowing out, 186 g of a crude solution were obtained containing 85% of 2-chloro-4-tert.butylbenzal bromide. The identity of the product was confirmed by mass spectroscopy and NMR spectra with the distilled product boiling at 115° C. under 0.2 torr.

COMPARATIVE EXAMPLE

In the same apparatus and under the conditions specified in Example 1, 296 g of p-tert.butyltoluene (2 mols) were chlorinated during the course of 3.5 hours by introducing 284 g (about 4.1 mols) of chlorine. After blowing out the hydrogen chloride, 415 g of crude product were obtained containing 31.05% total chlorine and, 20.85% saponifiable chlorine (saponification with alcoholic KOH and argentometric determination of ionogenic chlorine), from which a proportion of chlorine not capable of being split off of 10.20% could be calculated.

Approximately ⅓ of the total amount of organically bound chlorine was thus useless for the saponification to the aldehyde.

A very similar result was obtained by using the equivalent amount of sulfuryl chloride instead of chlorine.

What is claimed is:

1. A compound of the formula

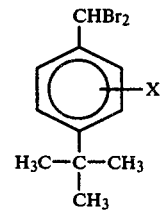

wherein X is hydrogen, fluorine, chlorine, bromine or iodine.

2. A compound as defined in claim 1, wherein X is hydrogen, fluorine, chlorine or bromine.

3. A compound as defined in claim 2, wherein X is hydrogen.

* * * * *